(12) United States Patent
Kaplan et al.

(10) Patent No.: US 6,235,933 B1
(45) Date of Patent: May 22, 2001

(54) PROCESS FOR PREPARING β-HYDROXYALKYLAMIDES

(75) Inventors: Andreas Kaplan; Rene Gisler, both of Chur; Albert Reich, Trin, all of (CH)

(73) Assignee: EMS-Chemie AG (CH)

( * ) Notice: Subject to any disclaimer, the term of this patent is extended or adjusted under 35 U.S.C. 154(b) by 0 days.

(21) Appl. No.: 09/322,414

(22) Filed: May 28, 1999

(30) Foreign Application Priority Data

May 28, 1998 (DE) .............................. 198 23 925

(51) Int. Cl.⁷ .................................. C07C 231/02
(52) U.S. Cl. ...................... 564/135; 564/134; 564/136; 564/137; 564/152; 564/201; 554/35; 554/36
(58) Field of Search ..................... 564/134, 135, 564/136, 137, 201, 152; 554/35, 36

(56) References Cited

U.S. PATENT DOCUMENTS 4,076,917 * 2/1978 Swift et al. ............................ 526/49
5,101,073    3/1992 Schlaefer .

\* cited by examiner

*Primary Examiner*—Shailendra Kumar
(74) *Attorney, Agent, or Firm*—Marshall & Melhorn, LLC

(57) ABSTRACT

The invention relates to a process for preparing a β-hydroxyalkylamide, in which alkyl esters are reacted with β-aminoalcohols in the absence of solvents and in the presence of basic catalysts, where, to improve the selectivity, the ratio of equivalents of ester to equivalents of amine is 1:1.001 to 8.

8 Claims, No Drawings

PROCESS FOR PREPARING β-HYDROXYALKYLAMIDES

BACKGROUND OF THE INVENTION

1. Field of the Invention

The present invention describes a process for preparing, purifying and isolating β-hydroxyalkylamides which are used as chemical intermediates and as chemical crosslinkers for carboxyl-functional polyesters and acrylates in solvent-based surface coatings and powder coatings. The use in powder coatings in particular places very high demands on the physical form of the β-hydroxyalkylamides. Only free-flowing powders, i.e. not soft, sticky or waxy powders, are suitable for use in powder coatings.

2. Description of the Prior Art

β-Hydroxyalkylamides are prepared by aminolysis of alkyl esters by β-aminoalcohols in the presence of basic catalysts such as sodium hydroxide or sodium methoxide, with the β-aminoalcohols being used in excess in most cases wing to the selectivity of the reaction. In the case of liquid β-hydroxyalkylamides, the unreacted β-aminoalcohols have to be removed from the reaction mixture before the β-hydroxyalkylamides can be used. In the case of solid β-hydroxyalkylamides, the isolation and purification of the β-hydroxyalkylamides is carried out either by crystallization in a solvent (J. Coat. Tech., 50(643), 49–55 (1978), U.S. Pat. No. 4,076,917, U.S. Pat. No. 4,727,111) or, specifically in the case of solid β-hydroxyethylamides, directly from the reaction mixture in a solvent-free slurry process (U.S. Pat. No. 5,101,073).

In the case of crystallization in solvents, the β-hydroxyalkylamides are generally either added to a hot solvent such as methanol and/or acetone or the solvent is added to the β-hydroxyalkylamides. After cooling the solution and crystallization, the β-hydroxyalkylamides are then filtered off and freed of solvent by drying. The yield is reduced by the solubility in the solvent used. In addition, the catalyst remaining in the reaction mixture can lead to undesirable secondary reactions, e.g. to diacetone alcohol when using acetone as solvent, which also results in losses in the recovery of the solvent used. It is also found that unreacted β-aminoalcohols also coprecipitate as undesired impurities in the crystallization and, in addition, β-aminoalcohols act as solubilizers which have an adverse effect on the crystallization. As a result, the yield of β-hydroxyalkylamides is reduced further.

Specifically the preparation of solid β-hydroxyethylamides can be carried out in the melt in a solvent-free slurry process. The slurry process (U.S. Pat. No. 5,101,073) is based on the equilibrium reactions which proceed in the preparation of β-hydroxyethylamides being shifted in the direction of the desired end product β-hydroxyethylamide, the desired β-hydroxyethylamide being precipitated from the melt by heating in a particular temperature range and the melt crystallizing as a result. In the case of substances where the desired β-hydroxyalkylamide does not precipitate from the melt, e.g. in the case of β-hydroxypropylamides, the slurry process fails. In addition, the slurry process is restricted to the use of equimolar amounts of alkyl esters and β-hydroxyethylamines. The slurry process gives, when equimolar amounts of dialkyl esters and β-hydroxyethylamines are used in the presence of basic catalysts such as sodium hydroxide or sodium methoxide, not only the desired monomeric β-hydroxyethylamides (I) but also, as by-products, dimers (II) and esteramides (III). Furthermore, the reaction product still contains β-hydroxyethlamine.

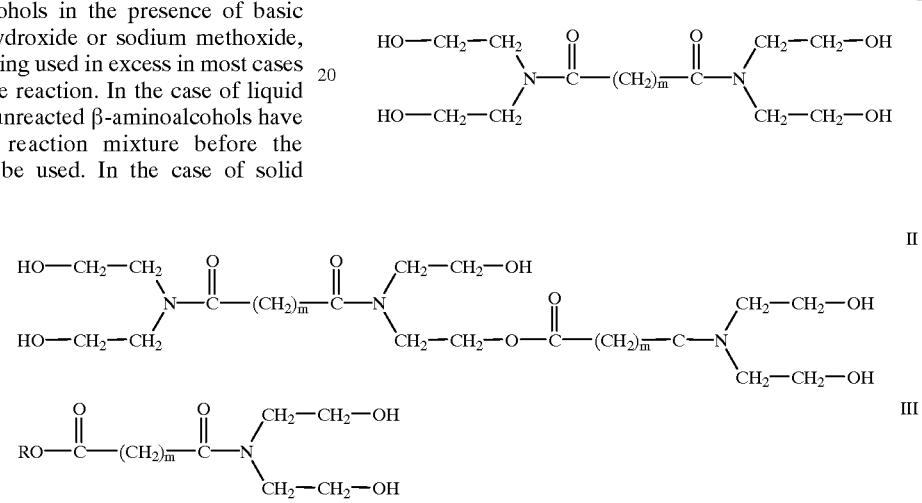

where m=0 to 10 and R is a C1–C5-alkyl group.

An important process step in the preparation of β-hydroxyalkylamides by aminolysis of alkyl esters by β-aminoalcohols in the presence of basic catalysts such as sodium hydroxide or sodium methoxide is the removal of unreacted β-aminoalcohols from the reaction mixture.

The separation of the excess β-aminoalcohol by dissolution in a suitable solvent such as methanol and subsequent removal of the β-aminoalcohol by means of an ion exchanger is known from the abovementioned literature. The desired β-hydroxyalkylamide is subsequently obtained by distilling off the solvent. However, this method is only suitable for the laboratory scale, since the removal of by-products by means of ion exchangers is only suitable for separating off small amounts of by-products. If a high proportion of by-products is present, i.e. when using a large excess of β-aminoalcohol in the reaction, such a process is very complicated and uneconomical in industry.

SUMMARY OF THE INVENTION

Starting from U.S. Pat. No. 5,101,073, it is an object of the present invention to provide a process which is improved in respect of the purity, yield and variability of the β-hydroxyalkylamides to be prepared, and also to provide for their use.

It has now surprisingly been found that in the preparation of β-hydroxyalkylamides by aminolysis of alkyl esters using an excess of β-aminoalcohols in the presence of basic catalysts such as sodium hydroxide or sodium methoxide, unreacted β-aminoalcohols can be removed directly from the reaction mixture by distillation after the basic catalyst has previously been destroyed, e.g. by means of an inorganic or organic acid such as hydrochloric acid or acetic acid. An excess of β-aminodialcohol in the preparation of the β-hydroxyalkylamides increases the selectivity of the reaction in the direction of the desired monomeric end product. This results in an even purer product, which in the case of solid β-hydroxyalkylamides is also reflected in an increase in the melting point and in an improved crystallization behavior. The β-hydroxyalkylamides prepared in this way have a very high purity. Suitable methods of removing the unreacted aminoalcohol are, apart from classical distillation at Th atmospheric pressure or under reduced pressure, particularly short-path, thin-layer and falling-film distillation, since these distillation methods are particularly gentle on the product, as a result of which undesirable secondary reactions caused by excessively long thermal stress can be avoided. If the catalyst is not destroyed, undesirable secondary reactions can take place during the distillation, for example the above-described diners (III) which have an adverse effect on the product properties of the β-hydroxyalkylamides, e.g. on the melting point or the crystallization behavior in the case of solid β-hydroxyalkylamides, can be formed again. A further advantage of destroying the catalyst is that the excess β-aminoalcohols can be recovered in pure form without by-products and can be utilized for further reactions. Liquid β-hydroxyalkylamides can be used directly without a further work-up step. In the case of solid β-hydroxyalkylamides, the end product is isolated either directly by crystallization of the reaction product or by crystallization from a solvent, since the abovementioned disadvantages no longer occur when crystallization is performed after destruction of the catalyst and removal of unreacted β-aminoalcohol. The process can be carried out batchwise and/or continuously.

DESCRIPTION OF THE PREFERRED EMBODIMENT

The invention provides a process for preparing β-hydroxyalkylamides (IV)

IV

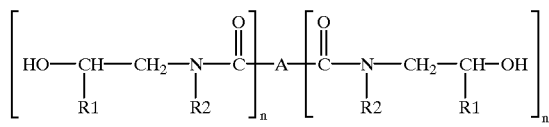

where A is a chemical bond or a polyvalent organic group or, when n=0, A can be hydrogen or a monovalent organic group, where the monovalent or polyvalent organic group is selected from among saturated or unsaturated (C1–C60) alkyl, cycloalkyl, aryl, carboxyalkenyl, alkoxycarbonyl-alkenyl or trialkylenamino groups, with lower alkenyl groups, i.e. alkenyl groups having from 1 to 20 carbon atoms, being preferred for the three last-named groups. R1 is hydrogen or a C1–C5-alkyl group, R2 is hydrogen, a C1–C5-alkyl group or:

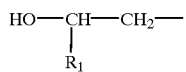

n is an integer from 1 to 10 and n' is an integer from 0 to 2. In the absence of solvents, alkyl esters are reacted with β-aminoalcohols in the presence of basic catalysts, where, to improve the selectivity, the ratio of equivalents of ester to equivalents of amine is 1:1.001 to 8. The aminoalcohol is preferably reacted in an excess of from 5 to 600%. This results in a ratio of equivalents of ester to equivalents of amine of from 1:1.05 to 1:6. Particular preference is given to a ratio of from 1:1.1 to 1:2. The alcohol formed in the reaction is removed from the reaction mixture at suitable temperatures, possibly under reduced pressure. After destruction of the basic catalyst, e.g. by means of a suitable inorganic or organic acid, the unreacted β-aminoalcohol is removed from the reaction mixture by distillation, preferably short-path, thin-layer or falling-film distillation. Liquid β-hydroxyalkylamides can be used without any further purification step. Solid β-hydroxyalkylamides are isolated by crystallization, possibly at elevated temperature, either directly from the reaction mixture or from a suitable solvent. The process can be carried out batchwise and/or continuously.

The process of the invention can be used to prepare β-hydroxyalkylamides of the formula IV:

IV

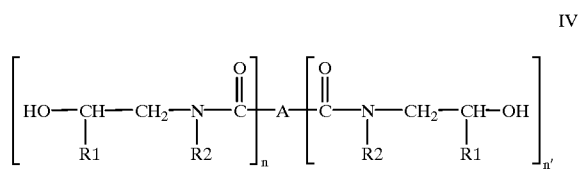

where A is a chemical bond or a monovalent organic group or, when n'=O, A can be hydrogen or a monovalent organic group polyvalent, where the monovalent or polyvalent organic group is selected from among saturated or unsaturated alkyl groups including substituted alkyl groups having from 1 to 60 carbon atoms, e.g. methyl, ethyl, propyl, butyl, pentyl, hexyl, heptyl, octyl, nonyl, decyl, eicosyl, triacontyl, tetracontyl, pentacontyl, hexacontyl; cycloalkyl groups such as cyclopentyl, cyclohexyl; aromatic hydrocarbon groups containing one or more rings, e.g. phenyl, naphthyl, etc.; unsaturated groups containing one or more ethylenic groups (—C=C—), e.g. ethenyl, 1-methylethenyl, 3-butenyl-1,3-diyl, 2-propenyl-1,2-diyl; carboxy-lower alkenyl groups such as 3-carboxy-2-propenyl, etc.; lower alkoxycarbonyl-lower alkenyl groups such as 3-methoxycarbonyl-2-propenyl, etc.; lower trialkylenamino groups such as trimethylenamino, triethylenamino, etc. R1 is hydrogen or a C1–C5-alkyl group such as methyl, ethyl, n-propyl, n-butyl, sec-butyl, tert-butyl, pentyl, etc. R2 is hydrogen, a C1–C5-alkyl group or:

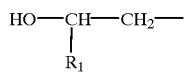

n is an integer from 1 to 10, preferably 1 or 2, and n' is an integer from 0 to 2.

Preference is given to β-hydroxyalkylamides of the formula IV in which A is an alkylene group, preferably C2 to C14. Particularly preferred β-hydroxyalkylamides are represented by the simplified formula V:

V

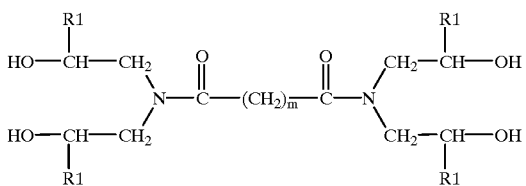

where m=2 to 14 and R1 is as defined above.

Specific examples of β-hydroxyalkylamides of the formula V are N,N,N',N'-tetrakis(2-hydroxyethyl)adipamide and N,N,N',N'-tetrakis(2-hydroxypropyl)adipamide. According to the invention, the β-hydroxyalkylamides (IV) are prepared without a solvent by aminolysis of esters of the formula VI using an excess of the amines of the formula VII at suitable temperatures of up to 200° C. in the presence of basic catalysts. The following equation illustrates the process:

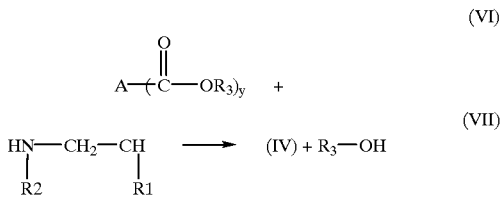

(VI)

(VII)

$\longrightarrow$ (IV) + R3—OH

A, R1 and R2 are as defined above. Y=1 to 20, R3 is an alkyl radical having 1–5 carbon atoms, e.g. methyl, ethyl, propyl, n-butyl, tert-butyl, pentyl, etc. The esters are known products which are prepared by esterification of the corresponding acids by means of standard esterification processes which are known to those skilled in the art. Preferred acids and mixtures thereof are oxalic acid, malonic acid, succinic acid, glutaric acid, adipic acid, pimelic acid, suberic acid, azelaic acid, sebacic acid, dodecanedioic acid, 1,4-cyclohexanedicarboxylic acid and their alkylsubstituted derivatives, etc. It is also possible to use dimeric and trimeric acids and their mixtures, prepared by polymerization of fatty acids, e.g. dimeric acid having 2 carboxyl groups, 36 carbon atoms and an approximate molecular weight of 565 or trimeric acid having 3 carboxyl groups, 54 carbon atoms and an approximate molecular weight of 850.

Examples of aminoalcohols of the formula VII according to the invention are 2-aminoethanol, 2-methylaminoethanol, 2-ethylaminoethanol, 2-n-propylaminoethanol, 2,2'-iminodiethanol, 2-aminopropanol, 2,2'-iminodiisopropanol, 2-aminocyclohexanol, 2-amino-cyclopentanol, 2-aminomethyl-2-methylethanol, 2-n-butylaminoethanol, 2-methylamino-1,2-dimethylethanol, 2-amino-2-methyl-1-propanol, 2-amino-2-methyl-1,3-propanediol, 2-amino-2-ethyl-1,3-propanediol, 2-amino-2-hydroxymethyl-1,3-propanediol and 1-amino-2-propanol.

The alcohols of the formula IX formed in the aminolysis (reaction of VI with VII) are removed from the reaction mixture by distillation, if desired under reduced pressure. For reasons of selectivity, a molar excess of β-aminoalcohols is necessary; the ratio of equivalents of ester to equivalents of amine is 1:1.001–8, preferably 1:1.05–6, particularly preferably from 1:1.1 to 1:2. This excess suppresses secondary reactions such as the formation of only partially aminated compounds when using esters of polybasic carboxylic acids, for example the formation of "half esters" of the formula X when using esters of polybasic carboxylic acids.

X

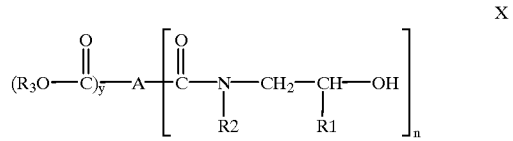

where A, R1, R2 and n are as defined above and y=1 to 5.

A further example of by-products whose formation can be suppressed by an excess of β-aminoalcohols is the compound of the formula XI, referred to as dimer, which occurs as by-product in addition to the pure monomeric β-hydroxyalkylamide of the formula IV. Monomer, dimer and β-aminoalcohol are in equilibrium.

XI

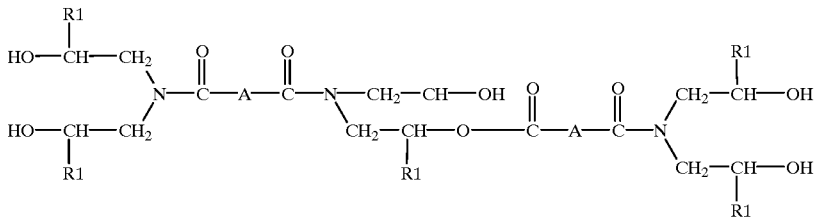

where A and R1 are as defined above.

Control of the water content of the reactants is also important for suppressing secondary reactions in aminolysis reactions. The water content of the reactants is typically less than 0.5%, preferably less than 0.1%, in order to prevent hydrolysis of the esters and a reduction in the catalyst activity.

Catalysts used are basic catalysts of the type alkali metal hydroxide or alkali metal alkoxide, including quaternary ammonium compounds, e.g. sodium hydroxide, tetramethylammonium hydroxide, sodium methoxide, sodium tert-butoxide, tetramethylammonium methoxide. The amount of catalysts used is from 0.001 to 5.0 mol %, based on the weight of the esters used.

After the reaction is complete, the catalyst is destroyed by, for example, addition of inorganic or organic acids such as hydrochloric acid or acetic acid. The excess β-aminoalcohol is subsequently removed from the reaction mixture by distillation, if desired under reduced pressure. If the catalyst is not removed prior to the distillation, by-products are again formed during the distillation, e.g. the dimer XI is again formed from the monomer IV in the presence of basic catalysts. This dimer formation can be suppressed by destruction of the catalyst prior to the distillation. Preferred types of distillation, especially in the case of relatively nonvolatile β-aminoalcohols which have a high boiling point, e.g. diisopropanolamine, are short-path, thin-film or falling-film distillation, since the β-hydroxyalkylamides are damaged least in these types of distillation owing to the brief thermal stress. Furthermore, it has been found that the ~-aminoalcohol which has been distilled off in this way can, owing to its high purity, be reused as starting component for further reactions without further work-up steps. Liquid β-hydroxyalkylamides can be processed further without a further work-up step. Solid β-hydroxyalkylamides are isolated by crystallization, possibly at elevated temperature, either directly from the reaction mixture of from a suitable solvent. In the crystallization, it is found that the purer the β-hydroxyalkylamides, the better and more rapidly they crystallize. The process can be carried out batchwise and/or continuously.

The preparation and the properties of the β-hydroxyalkylamides prepared according to the invention are illustrated below by way of example.

COMPARATIVE EXAMPLE

A mixture of 133.00 g of diisopropanolamine and 1.62 g of sodium methoxide are heated to 100° C. under nitrogen in a 500 ml glass apparatus. After application of a reduced pressure of 300 mbar, 174.00 g of dimethyl adipate are added dropwise over a period of one hour and the methanol liberated during the reaction is continuously distilled off. After an after-reaction time of 1 hour, the product is drained into an aluminium basin.

EXAMPLE

A mixture of 239.40 g of diisopropanolamine and 1.62 g of sodium methoxide are heated to 100° C. under nitrogen in a 500 ml glass apparatus. After application of a reduced pressure of 300 mbar, 174.00 g of dimethyl adipate are added dropwise over a period of one hour and the methanol liberated during the reaction is continuously distilled off. After an after-reaction time of 1 hour, 1.80 g of acetic acid are added to the reaction mixture and the excess diisopropanolamine is subsequently removed in a short-path distillation apparatus KDL-5 from UIC at a reduced pressure of 5 mbar and a wall temperature of 130° C. The amine-free reaction mixture is subsequently crystallized at 90° C. and the crystal slurry is then drained into an aluminium basin.

TABLE 1

|  | Comparative Example | Example |
|---|---|---|
| Nature | highly viscous, yellow liquid. After storage for a week becomes a waxy, sticky mass. | Free-flowing white crystals |
| Melting point [° C.] | not able to be determined | 118 |
| Monomer content [%] | 73 | 97.9 |
| Dimer content [%] | 15 | 2.1 |
| Half ester [%] | 3 | — |
| Diisopropanolamine [%] | 9 | — |

What is claimed is:

1. Process for preparing β-hydroxyalkylamides of the general formula IV:

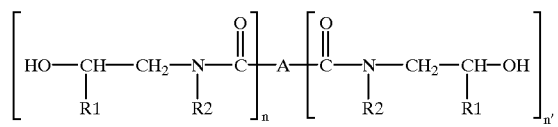

where A is a chemical bond or a polyvalent organic group or, if n'=0, hydrogen or a monovalent group, where the monovalent or polyvalent organic group is selected from amonG saturated or unsaturated (C1–60) alkyl, cycloalkyl, aryl, carboxyalkenyl, alkoxycarbonylalkenyl or trialkylenamino groups, and R1 is hydrogen or a C1–C5-alkyl group and R2 is hydrogen, a C1–C5-alkyl group or:

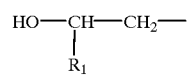

and n is an integer from 1 to 10 and n' is an integer from 0 to 2, in which the corresponding alkyl esters are reacted with the corresponding β-aminoalcohols in the absence of solvents and in the presence of a basic catalyst and the resulting alcohol is removed, characterized in that, to improve the selectivity, the ratio of equivalents of ester to equivalents of amine is 1:1.001–8, the basic catalyst is destroyed after the aminolysis and the unreacted aminoalcohol is removed by distillation.

2. Process according to claim 1, wherein the ratio is from 1:1.05 to 1:6.

3. Process according to claim 1, wherein inorganic acids, preferably hydrochloric acid or organic acids, preferably acetic acid or phenylacetic acid, are used for destroying the basic catalyst.

4. Process according to claim 1, wherein basic catalysts of the type alkali metal hydroxide or alkoxide, including quaternary ammonium compounds, e.g. sodium hydroxide, tetramethylammonium hydroxide, sodium methoxide, sodium tert-butoxide or tetramethylammonium methoxide, are used.

5. Process according to claim 1, wherein the amount of catalyst used is from 0.001 to 5.0 mol %, based on the amount of ester.

6. Process according to claim 1, wherein the alcohol formed in the reaction is removed at a temperature of 50–150° C. and a reduced pressure of from 650 mbar to 0.1 mbar.

7. Process according to claim 1, whereby it is carried out continuously.

8. Process according to claim 1, wherein preferred β-hydroxyalkylamides of the formula IV are N,N,N',N'-tetrakis(2-hydroxyethyl) adipamide and N,N,N',N'-tetrakis (2-hydroxypropyl)adipamide.

* * * * *